(12) United States Patent
Faxe et al.

(10) Patent No.: US 6,471,052 B2
(45) Date of Patent: Oct. 29, 2002

(54) PACKAGE AND A CASE FOR CONTACT LENSES AND METHOD FOR APPLYING A CONTACT LENS IN AN EYE

(75) Inventors: Thomas Faxe, Linde Allé 33, 3120 Dronning Mølle (DK); Per Faxe, Svinggårdsvej 1, 3100 Hornbaek (DK)

(73) Assignees: Thomas Faxe, Dronning Mølle (DK); Per Faxe, Hornçk (DK)

( * ) Notice: Subject to any disclaimer, the term of this patent is extended or adjusted under 35 U.S.C. 154(b) by 0 days.

(21) Appl. No.: 10/053,824

(22) Filed: Jan. 22, 2002

(65) Prior Publication Data

US 2002/0063068 A1 May 30, 2002

Related U.S. Application Data

(63) Continuation of application No. PCT/DK00/00409, filed on Jul. 18, 2000.

(30) Foreign Application Priority Data

Jul. 23, 1999 (DK) .......................................... 1999 01060

(51) Int. Cl.⁷ .............................................. B65D 85/38
(52) U.S. Cl. ....................... 206/5.1; 206/205; 220/4.27; 294/1.2
(58) Field of Search ............................ 206/5, 5.1, 205, 206/210; 220/4.27; 294/1.2

(56) References Cited

U.S. PATENT DOCUMENTS

| | | | |
|---|---|---|---|
| 2,663,450 A | * 12/1953 | Bourcart | 220/4.27 |
| 2,940,589 A | * 6/1960 | Silverman | 206/5.1 |
| 3,552,548 A | * 1/1971 | Wallestad et al. | 220/4.27 |
| 4,036,357 A | * 7/1977 | Czelen | 206/5.1 |
| 4,294,924 A | * 10/1981 | Pepicelli et al. | 220/4.27 |
| 4,429,786 A | 2/1984 | Hucal | 206/5.1 |
| 5,069,494 A | 12/1991 | Reinson et al. | 294/1.2 |
| 5,695,049 A | 12/1997 | Bauman | 206/5.1 |
| 5,879,038 A | 3/1999 | Morgan | 294/1.2 |

FOREIGN PATENT DOCUMENTS

| | | |
|---|---|---|
| GB | 2 328 924 A | 3/1999 |
| WO | WO 99/21519 | 5/1999 |

* cited by examiner

Primary Examiner—Jim Foster
(74) Attorney, Agent, or Firm—Winston & Strawn

(57) ABSTRACT

A magazine for keeping a number of contact lenses kept in each their fluid-filled chamber is disclosed. Each chamber has a supporting wall with a concave face fitting the convex side of the contact lens. The supporting walls are placed in a row along the axis of the concave faces, each supporting wall is detachably separating consecutive chambers. The magazine contains several contact lenses at a time and constitutes an inexpensive and expedient package. When a contact lens is applied in an eye, the magazine is placed with the skirts pointing downwards. The lowest support is then removed from the rest of the magazine with a finger stuck into the skirt of the supporting wall. Due to the moisture present, the contact lens is adhering to the supporting wall which together with its skirt is now transformed into an effective applicator for applying a contact lens in an eye.

15 Claims, 6 Drawing Sheets

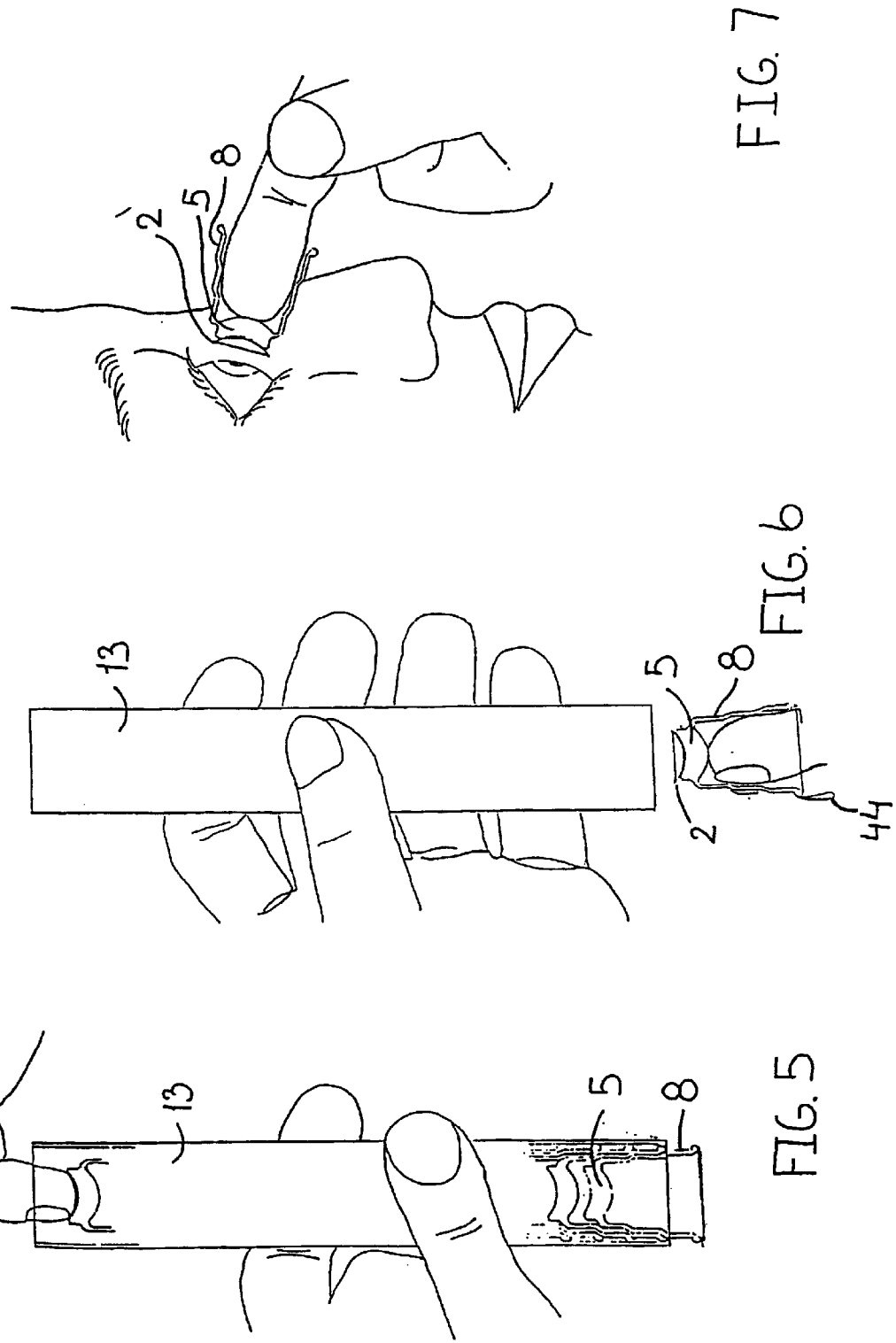

PACKAGE AND A CASE FOR CONTACT LENSES AND METHOD FOR APPLYING A CONTACT LENS IN AN EYE

CROSS-REFERENCE TO RELATED APPLICATION

This application is a continuation of the national stage of PCT Application No. PCT/DK00/00409, filed Jul. 18, 2000, the content of which is expressly incorporated herein by reference thereto.

FIELD OF INVENTION

The invention relates to a magazine for keeping a number of contact lenses and of the kind where the contact lenses are kept in each their fluid-filled chamber, each chamber having a supporting wall with a concave face fitting the convex side of the contact lens, the supporting walls are placed in a row after each other along the axis of the concave faces, each supporting wall detachably separating two consecutive chambers, and each chamber made with a convex face a distance above the concave face.

BACKGROUND OF THE INVENTION

There are different packages for contact lenses. In a common kind, a chamber for a contact lens is made in a thin sheet of plastic. The chamber is furthermore filled with a saline solution and sealed by means of a sealing foil of coated aluminium. When the contact lens is to be used, the sealing foil is pulled off the chamber sheet, and the contact lens is poured out into the hand together with the saline solution, the lens is turned over and placed on the tip of a finger which is then used for applying the contact lens in an eye.

In some cases, a row of chamber sheets are joined transversely by means of a piece of sealing foil spanning the entire row. When the sealing foil is pulled off one chamber sheet, this sheet can be separated from the rest in the row and used as mentioned above.

PCT Publication No. WO 99/21519, which is expressly incorporated herein by reference, relates to another package for a contact lens. As shown therein, the contact lens and the saline solution are in a chamber which is defined by a cup and a fingerstall which are detachably connected to each other. On the end of the fingerstall is a concave hollow fitting the convex side of the contact lens.

When a contact lens is to be applied in an eye, the package is first faced in such a way that the contact lens will lie in the concave hollow of the fingerstall. Then the cup is removed. This causes the saline solution runs out. The contact lens, which due to the moisture present is adhering in the concave hollow of the fingerstall with a modest adhesive force, is now applied in the eye with a finger stuck into the fingerstall. The package is then discarded. This package is thus transformed upon removal of the cup into an effective applicator for applying a contact lens in an eye cleanly and sterilely.

The known package is, however, comprised of two parts and is therefore rather expensive to manufacture. The package considerably increases the expenses which a person using contact lenses frequently has to pay.

Furthermore, each package only contains one single contact lens. For practical reasons, the packages have to be distributed in joint packages with several one-piece packages. The user's expenses to packaging are thereby further increased.

UK Patent Application No. GB 2328924 relates to a magazine that is detachably made up of a number of containers each containing a contact lens. The chambers formed by these containers are, however, not arranged to keep the contact lenses dimensionally stably in place during storage. The magazine and each of its containers are therefore not suited as applicator for applying a contact lens in a user's eye. For the inevitable handling of the magazine will cause the contact lenses to become crimped, and they will have to be straightened and applied with a finger.

SUMMARY OF THE INVENTION

The invention relates to a magazine for holding a plurality of contact lenses that includes a plurality of fluid-filled chambers with each chamber having a supporting wall with a concave face corresponding to the convex side of each contact lens, wherein the supporting walls are placed in a row after each other along an axis of the concave faces, each supporting wall detachably. separates two consecutive chambers, and each chamber has a convex face a sufficient small distance above the concave face to keep the contact lens in the chamber dimensionally stably in place between the two faces, and a skirt on each supporting wall extending long the axis in the opposite direction of the concave face of the supporting wall, wherein each skirt is detachably connected to at least the first supporting wall in this direction and/or to the skirt of this wall.

The convex face of the supporting wall has a shape that is substantially complementary to the concave face of the contact lens and is disposed on the side of the supporting wall that faces opposite the concave face. The concave face passes into a curvature along the periphery. Each chamber has two supporting walls and at least part of a skirt. The skirts may be detachably pressed or screwed together. The magazine may be placed axially displaceably in a supporting tube. The partition isolating a pocket from the rest of the chamber is placed in each chamber and at least one through hole is disposed in the wall around this pocket that is closed when the chamber is detachably closed and that is opened when the chamber is opened.

The invention also relates to a package for keeping a contact lens that includes a supporting wall with a concave face fitting the convex side of the lens, a skirt made on the supporting wall and extending along an axis in the opposite direction of the concave face, and a cap that detachably joins the skirt. A number of packages may be assembled into a magazine with the cap of each package pressed into the skirt of an adjacent package.

The invention also relates to a method for taking a contact lens out of a magazine which is displaceably placed in a supporting tube and includes a number of supporting walls with skirts detachably pressed together in a row, and together defined a number of chambers. The method includes pushing on the top supporting wall in the row so that the skirt of the lowest supporting wall will be extending at least partly out of the bottom opening of the tube and removing the lowest supporting wall with the contact lens in the overlying chamber from the supporting tube so that the contact lens, which due to the moisture present is adhered to the supporting wall, is applied to the eye, and so that the supporting wall is then placed at the top in the supporting tube.

The invention further relates to a method for applying a contact lens in a package to an eye that includes orienting the package row with the caps pointing relatively upwards, removing the top cap to provide an uncovered chamber, guiding the package row up towards the eye so that the contact lens in the uncovered chamber is applied, and pressing the cap in place on the supporting wall which is then placed at the bottom in the package row with the cap pressed into the skirt of the overlying supporting wall.

BRIEF DESCRIPTION OF THE DRAWINGS.

The invention will be explained in greater detail below, describing only exemplary embodiments with reference to the drawings, wherein:

FIG. 5 shows the magazine in FIG. 1 in a first application step;

FIG. 6 shows the magazine in FIG. 1 in a second application step;

FIG. 7 shows the magazine in FIG. 1 in a third application step;

DETAILED DESCRIPTION OF THE INVENTION

Figure 1:
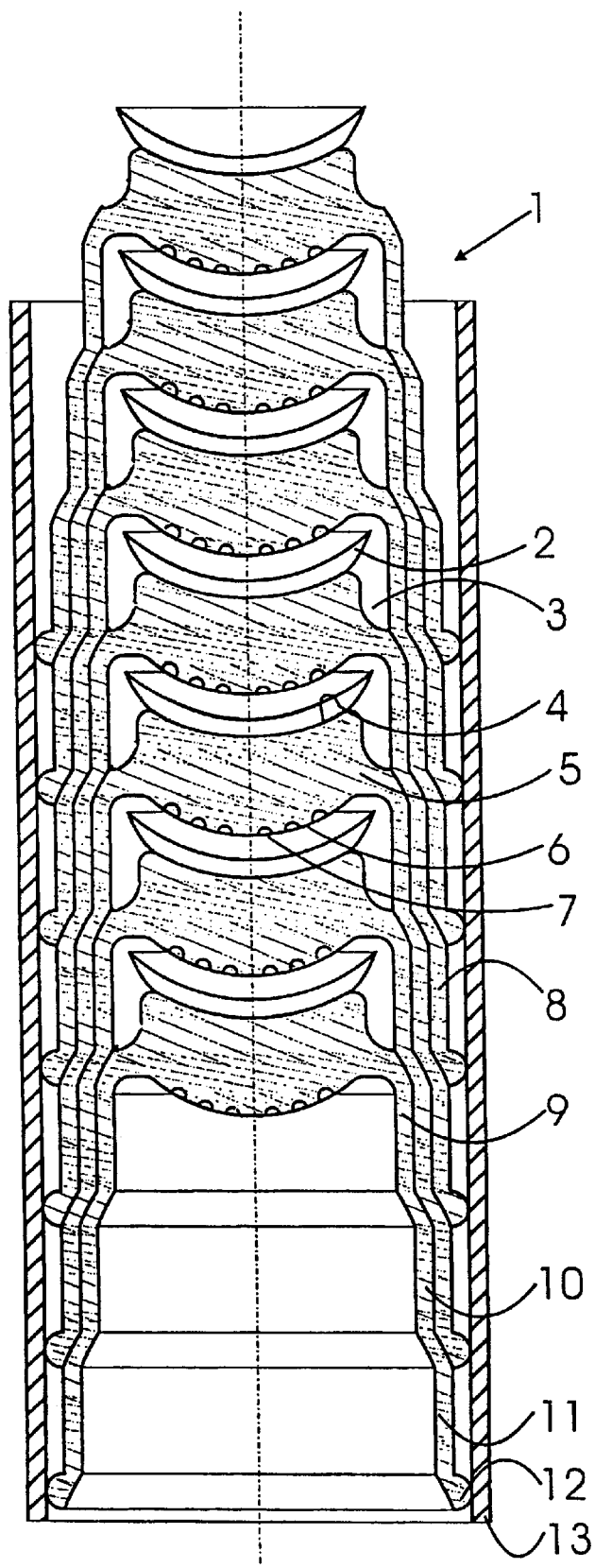
FIG. 1 is an axial view of a first embodiment of a magazine according to the invention for keeping.a number of contact lenses.

One feature of the invention is that the distance between the concave and convex faces of each chamber is so small that the contact lens is kept dimensionally stably in place in the chamber between the two faces.

Thereby, it is ensured that the normally soft and very flexible contact lens is immediately ready for being applied in a user's eye. That is to say that the contact lens does not have to be straightened out first because it has become more or less crimpled while being kept in its chamber. Such a straightening out would furthermore be difficult and involve the risk of the contact lens getting damaged or destroyed. A deformed contact lens can furthermore damage an eye.

The convex and concave faces of a contact lens are not identical. When the convex face has a shape complementary to the concave face of the contact lens, the shape of the contact lens is carefully kept during storage in the chamber even if the magazine during this is subjected to rather rough handling.

By letting the concave face of each supporting wall pass into a curvature along the periphery, the advantage is obtained in that a circumferential groove is not pressed into the soft contact lens during storage in the chamber and handling of the magazine.

In an advantageous embodiment a skirt can be made on each supporting wall, the skirt is extending along the axis in the opposite direction of the concave face of the supporting wall, and the skirt can be detachably connected to at least the first supporting wall in this direction and/or to the skirt of this wall, whereby each chamber can be defined by two supporting walls and by at least part of a skirt.

The single parts of the magazine constitute jointly an inexpensive and expedient package, and separately the parts constitute an effective applicator which upon removal from the magazine immediately can be used for applying a contact lens in a user's eye, the contact lens already having the correct shape as mentioned above.

The single parts of the magazine or applicators can advantageously be joined in a row by detachably pressing or screwing the skirts together.

The assembled magazine can furthermore be placed axially displaceably in a tube. When the tube is orientated with the skirts pointing downwards, the magazine can then be pushed downwards in the tube with a press of a finger at the top so that the skirt of the lowest part is projecting from the bottom opening of the tube. The lowest part can then be removed with a finger in the skirt and used as applicator. Afterwards, the now used part is added to the magazine in the other end of the tube where it constitutes a basis for continuously being able to press the magazine downwards with a finger and guide a new lower part forward for use as applicator.

When the lowest single part or applicator is removed from the magazine in the vertical position of this magazine with downwards pointing skirts, the fluid in the overlying chamber runs out on the fingers and the surrounding. With a view to eliminate this soiling, a pocket can in an advantageous, embodiment be arranged in the chamber above the contact lens with through side openings which are closed when the chamber is closed. When the lowest single part or applicator is now removed from the magazine, the fluid runs from the chamber into the pocket via the side openings instead of soiling the surroundings.

The invention also relates to a package for keeping a contact lens and comprising a supporting wall with a concave face fitting the convex side of the contact lens, a skirt made on the supporting wall and extending along the axis in the opposite direction of the concave face of the supporting wall, and a cap for defining a chamber for keeping the contact lens at detachable joining with the skirt of the supporting wall, whereby a number of packages are joined to a magazine with the cap of each package pressed into the skirt of the succeeding package.

This package has the advantage of being able to be a constituent part of a magazine and furthermore function individually as an independent package. The package can thus expediently be marketed and kept in form of a magazine that the user can then divide as required. For example, if the user in a given situation merely wishes to bring a couple of packages in stead of having to bring the entire magazine.

A magazine of these packages forms in itself a handle for holding onto during application of a contact lens. During application, the magazine is orientated with the caps facing upwards, the topmost cap is removed, and the contact lens in the uncovered chamber is applied by taking the magazine up towards the eye with the fingers.

The used package with attached cap is then pressed in place at the bottom of the magazine which thereby always is long enough to be able to form a convenient handle for the fingers during an application operation.

Referring now to the drawings, FIG. 1 shows a magazine 1 according to the invention with, in this case, seven contact lenses 2 placed in each chamber 3 filled with saline solution. Each contact lens rests in a concave hollow 4 in a supporting wall 5 which, as it can be seen, is shared by two consecutive chambers. The concave hollow 4 fits the convex side of the contact lens, and the hollow thus supports the soft contact lens along this side while keeping the shape of the contact lens.

On the underside of each supporting wall is furthermore made a convex projection 6 fitting the concave side of the contact lens. The soft contact lens is kept dimensionally stably in place between the concave hollow 4 and the overlying convex projection 6, thus avoiding crimpling of the contact lens if the magazine is in a position different from the one shown.

In the convex projection 6 of the supporting wall is made a number of recesses 7 that causes the adhesive force, due to the moisture present, between the contact lens 2 and the concave hollow 4 to be greater than between the contact lens and the convex projection 6.

On each supporting wall is made a skirt 8 extending in the opposite direction of the concave hollow 4 in the supporting wall. In this case, the skirt has a first 9, a second 10, and a third 11 stepping and also a lower bead 12.

The skirts of two consecutive supporting walls are detachably pressed together, the first and second stepping 9, 10 of each skirt being pressed into the second and third stepping 10, 11 of the overlying supporting wall.

The magazine 1 is thus formed by detachably pressing the skirts of a number of supporting walls together in a row. This row is again placed in a supporting tube 13 in such a way that the beads 12 can be slidably displaced along the inside of the tube.

In FIG. 1, the magazine 1 is in a state in which it in its entirety is ready to be used as applicator as will be described in detail below.

Figure 2:
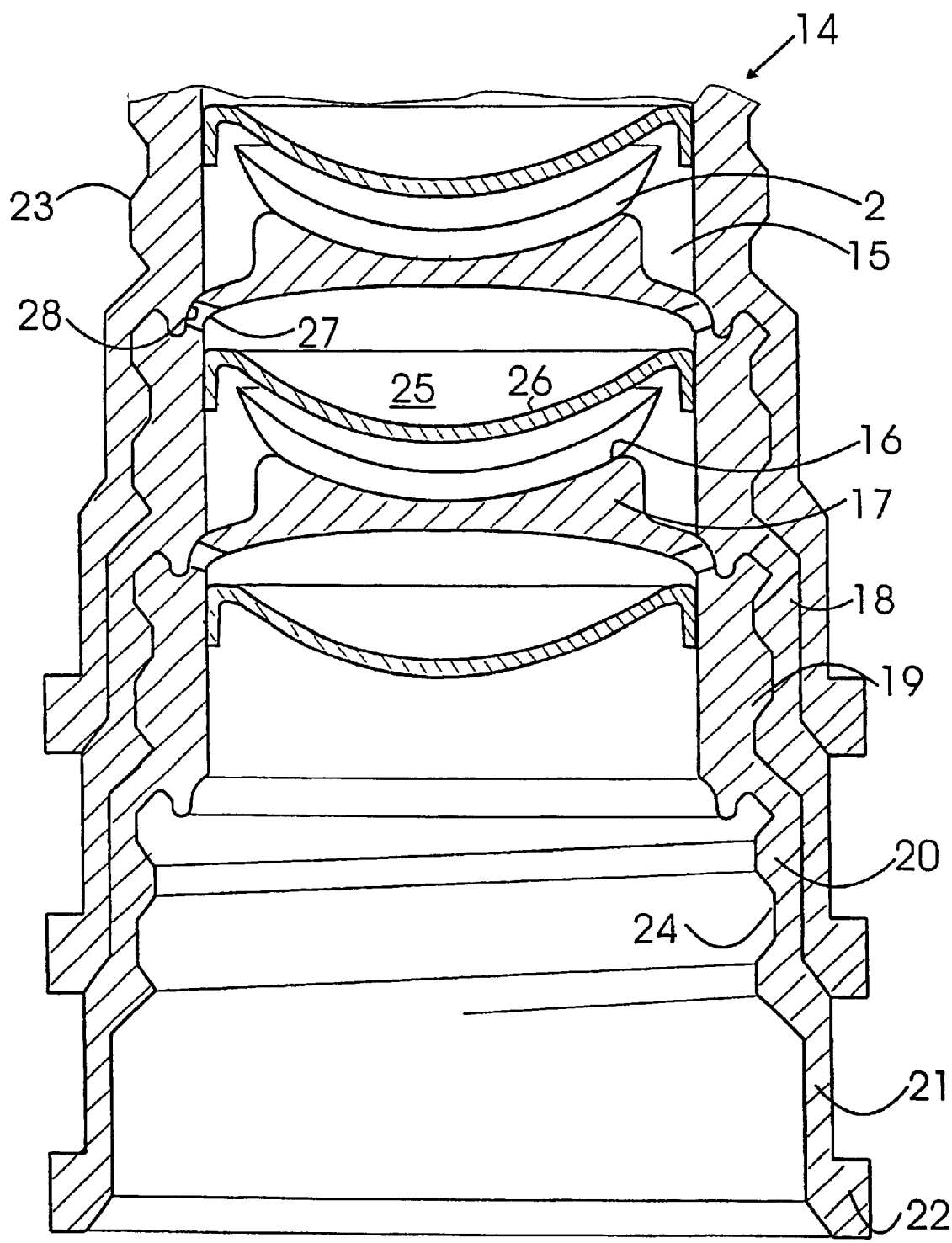
FIG. 2 is an axial fractional view of a second embodiment of a magazine according to the invention for keeping a number of contact lenses.

FIG. 2 is a fractional view of a second embodiment of a magazine 14 according to the invention. The contact lenses 2 are placed in each their chamber 15. Each contact lens rests in a concave hollow 16 in a supporting wall 17 which is shared by two consecutive chambers.

On each supporting wall is made a skirt 18 extending in the opposite direction of the concave hollow 16 in the supporting wall. In this case, the skirt has a first 19, a second 20, and a third 21 stepping, and also a lower bead 22.

On the first section 19 of the skirt is made an external thread 23 and in its second section 20 a corresponding internal thread 24.

The skirts of two consecutive supporting walls are detachably joined by screwing the external thread 23 of one of the skirts into the internal thread 24 of the overlying skirt. This joint is stable in itself, and a supporting tube is therefore not needed.

When a contact lens is to be used, the magazine is placed vertically with the skirts pointing downwards, as shown in FIG. 2, and the skirt of the lowest supporting wall is screwed out of the magazine after which the contact lens can be applied in the eye with a finger stuck into the skirt.

The contact lens is kept in the chamber in a saline solution which other things being equal will run out and soil the user's fingers and the surroundings.

In the embodiment shown, a pocket 25 is isolated in the chamber above the lens by means of a partition 26. In the wall around this pocket, a number of through holes 27 are made that in the assembled state of the magazine are kept tightly sealed by a lower face 28 on the first stepping 19 of the overlying skirt.

When the skirt of the lowest supporting wall is now screwed out of the magazine, the saline water runs from the overlying chamber down into the pocket 25 via the through holes 27 in the wall of this chamber instead of running out and soiling the user's fingers and the surroundings.

The partition 26 is shaped as a convex projection fitting the concave side of the contact lens in order to thereby keep the soft contact lens dimensionally stably in place in the space between the partition 26 and the concave hollow 16 of the supporting wall 17.

Figure 3:
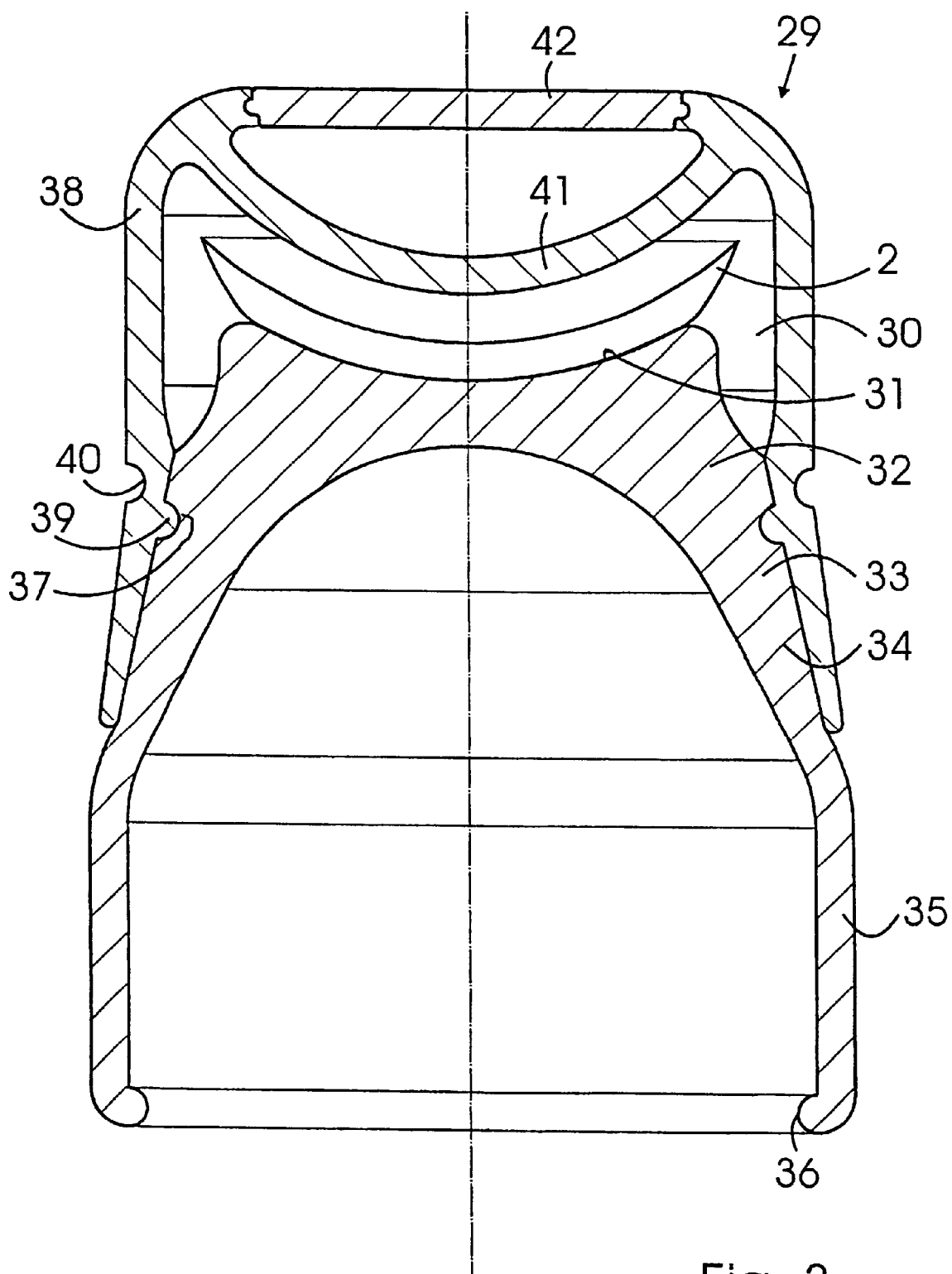
FIG. 3 is an axial view of a package according to the invention for keeping a contact lens.

FIG. 3 shows an embodiment of a singular package 29, wherein a contact lens 2 is placed in a chamber 30 filled with saline water on, in the position shown, a concave hollow 31 in a supporting wall 32. In the direction oppositely of the concave hollow, the supporting wall passes into a skirt 33 which has a first section 34 and a second section 35 ending in an inwardly pointing bead 36 at the bottom. A circumferential groove 37 is made in the first section of the skirt During storage of the contact lens, the chamber 30 of the package is kept closed by means of a cap 38 having an inwardly pointing bead 39 for detachably engaging the circumferential groove 37 on the first section of the skirt. A circumferential groove 40 is made on the cap fitting the inwardly pointing bead 36 on the second section 35 of the skirt.

The base of the cap is shaped as a convex projection 41 fitting the concave side of the contact lens in order to to keep the soft contact lens dimensionally stably in place between this projection and the concave hollow 31 of the supporting wall.

The wall thickness of the projection 41 is relatively thin in order to avoid the use of any more material than is absolutely.necessary for manufacturing the cap. The formed cavity above the base of the cap is expediently closed with a lid 42.

Figure 4:
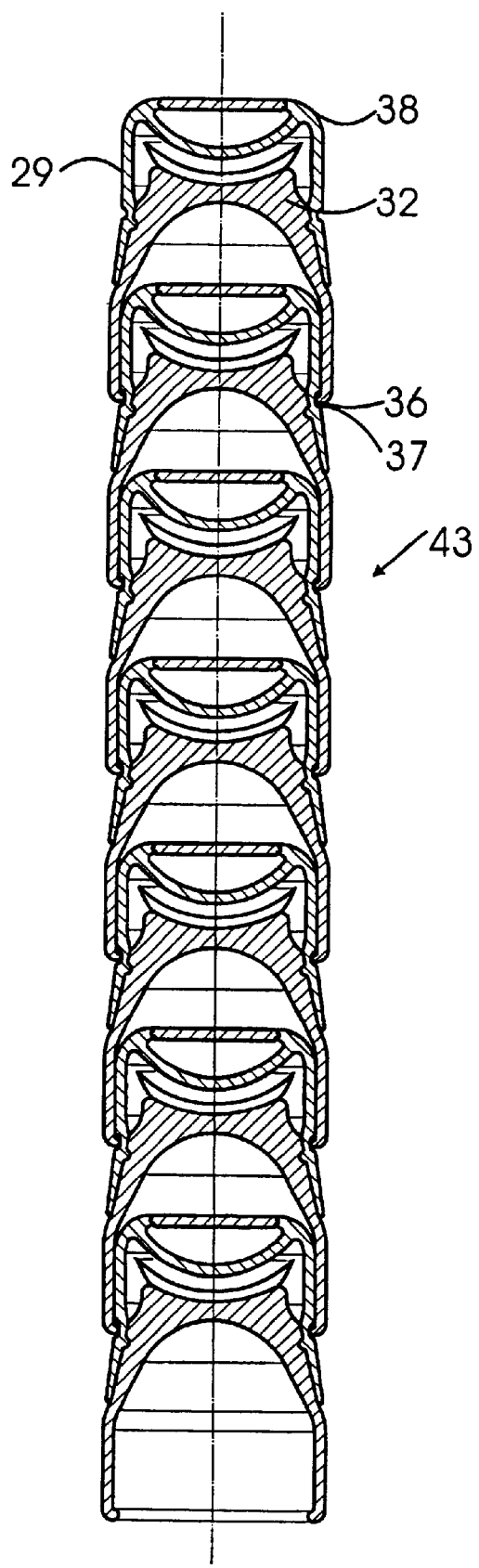
FIG. 4 is an axial view of a magazine made up of a number of the packages in FIG. 3.

As shown in FIG. 4, a total of seven of the packages in FIG. 3 are in this case joined in a magazine 43, the lower bead 36 of each skirt being detachably engaged with the circumferential groove 37 of the cap 38.

In this state, the package is inexpensive and convenient to distribute and store. When needed, one or several packages can be broken off the magazine and used singularly. The assembled magazine can also be used as an expedient activator, with the top cap being removed and thus uncovering the top contact lens. This contact lens is retained with a modest adhesive force in the hollow 31 of the supporting wall by the moisture present and can now be applied in the eye, as the user during this is holding the magazine with his fingers.

After application, the package is pushed up at the bottom of the magazine with attached cap. In all of the seven applications which are possible with the magazine in FIG. 4, the magazine will therefore conveniently maintain one and the same length.

FIGS. 5–7 show how the magazine in FIG. 1 is used for applying a contact lens in an eye.

In FIG. 5, the user is using a finger to pushing the row of supporting walls and their skirts downwards in the supporting tube 13 with the beads sliding against the inside of the tube until the lowest skirt 8 is projecting partly out at the bottom of the supporting tube.

In FIG. 6, the user has now stuck a finger into the skirt 8 and freed the supporting wall 5 with its skirt 8 from the magazine.

The saline solution in the chamber, in which the contact lens was, has now run out as indicated with the drops 44, and the moisture from this solution causes the contact lens 2 to adhere in the concave hollow 4 of the supporting wall 5 with a modest adhesive force.

In FIG. 7, it is seen how the application of the contact lens in the user's eye finally takes place. The supporting wall and its skirt now function as an effective applicator for cleanly and sterilely applying the contact lens in the user's eye.

Afterwards, the used applicator is placed at the top in the supporting tube 13 where it now forms abutment for being able to push the skirt of the next applicator a little out of the bottom opening of the supporting tube.

Figure 9:
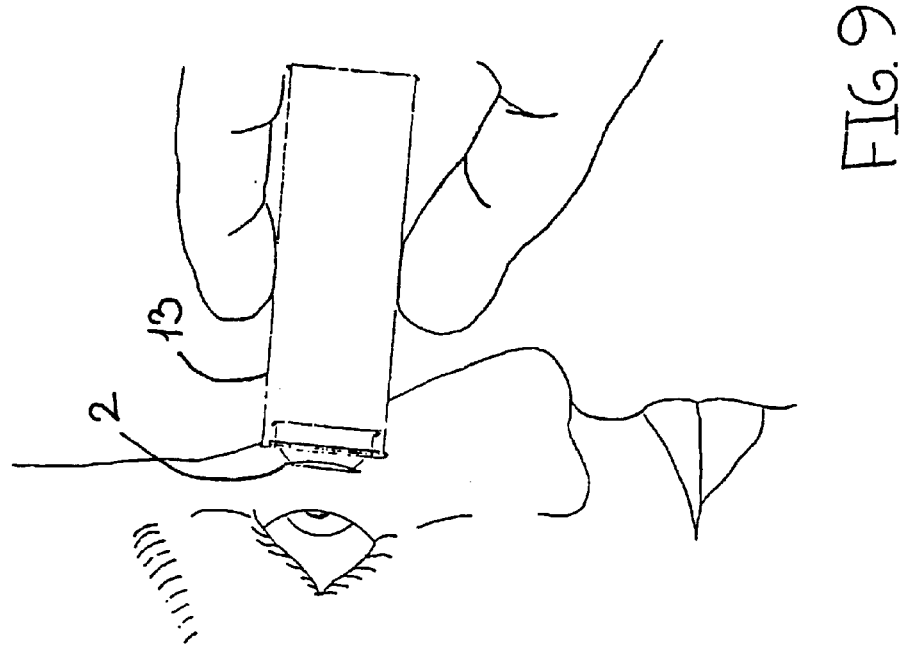
FIG. 9 shows the magazine in FIG. 8 in a second application step.
Figure 8:
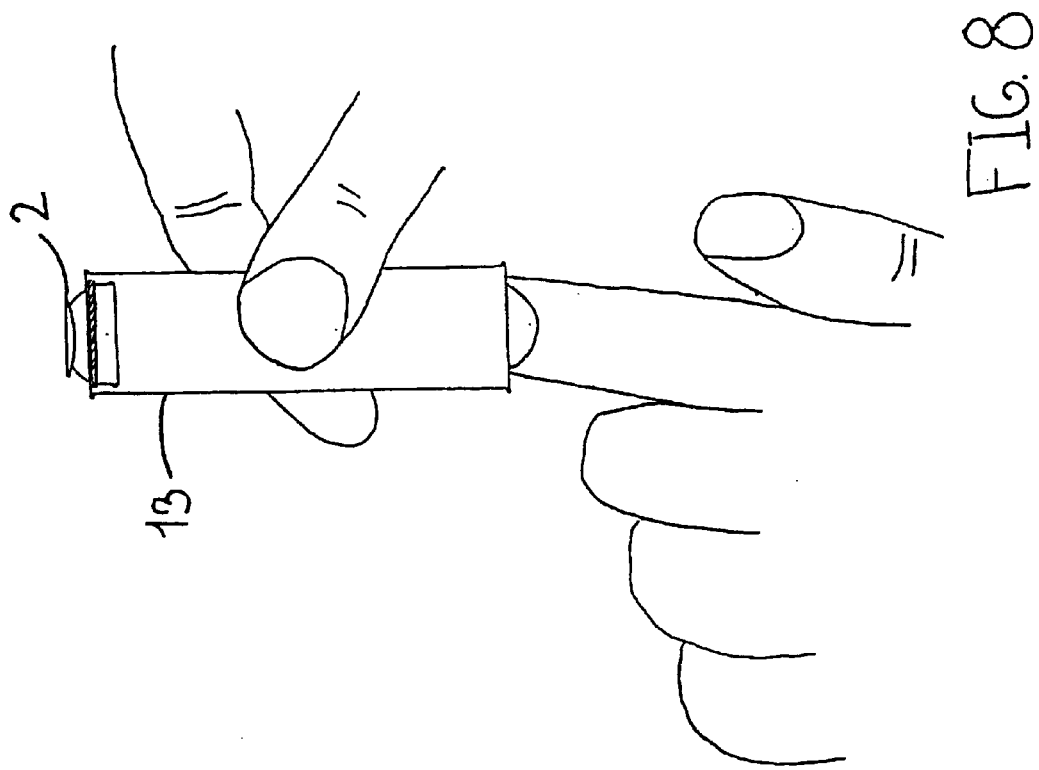
FIG. 8 shows the magazine in FIG. 1 used as an applicator in a first application step.

FIGS. 8–9 show how the magazine in FIG. 1 can be used as applicator. Normally, the top contact lens 2 in the row will be in a closed chamber 3 filled with saline water, the chamber being defined by two supporting walls 5 and the skirt 8 on the top supporting wall which is without contact lens. Alternatively, the top chamber can be closed with a separate cap.

In FIG. 8, the user is with a finger pushing the row of supporting walls and their skirts upwards in the supporting tube 13 with the beads sliding against the inside of the tube until the top two supporting walls are projecting more or less out at the top in the supporting tube 13.

Then, the top supporting wall is removed so that the contact lens 2 in the now open chamber 3 is uncovered. This situation is also clearly shown in FIG. 1.

The saline solution has run out while the remaining moisture on the concave hollow 4 of the supporting wall 5 makes the contact lens adhere on the supporting wall with a modest adhesive force.

In FIG. 9, the user is holding the supporting tube 13 with his fingers and guiding it up towards the eye with the adhering contact lens which in this way is applied in the eye.

The supporting wall which before was removed at the top in the supporting tube is used again, as it is put in at the bottom in the supporting tube where it now forms basis for once more being able to push the magazine upwards in the supporting tube with a finger, as shown in FIG. 8.

When the magazine is used in this way, i.e., directly as applicator, there is no need for a long skirt for sticking a finger into and use as fingerstall. The skirts can therefore be short, and this involves the significant advantage in that the one and same supporting tube can contain a very large number of supporting wall with short skirts. Thereby, the costs for packing the contact lenses are reduced considerably.

It is to be understood that the invention is not to be limited to the exact configuration as illustrated and described herein. Accordingly, all expedient modifications readily attainable by one of ordinary skill in the art from the disclosure set forth herein, or by routine experimentation therefrom, are deemed to be within the spirit and scope of the invention as defined by the appended claims.

What is claimed is:

1. A magazine for holding a plurality of contact lenses comprising a plurality of fluid-filled chambers, each chamber comprising:
    a supporting wall with a concave face corresponding to the convex side of each contact lens, wherein the supporting walls are placed in a row after each other along an axis of the concave faces, each supporting wall detachably separates two consecutive chambers, and each chamber has a convex face a sufficient small distance above the concave face to keep the contact lens in the chamber dimensionally stably in place between the two faces; and
    a skirt on each supporting wall extending along the axis in the opposite direction of the concave face of the supporting wall, wherein each skirt is detachably connected to at least the first supporting wall in this direction and/or to the skirt of this wall.

2. The magazine according to claim 1, wherein the convex face has a shape that is substantially complementary to the concave face of the contact lens.

3. The magazine according to claim 1, wherein the convex face is disposed on the side of the supporting wall that faces opposite the concave face.

4. The magazine according to claim 1, wherein the concave face of each supporting wall passes into a curvature along the periphery.

5. The magazine according to claim 1, wherein each chamber comprises two supporting walls and at least part of a skirt.

6. The magazine according to claim 1, wherein the skirts of the supporting walls are detachably pressed or screwed together.

7. The magazine according to claim 1, wherein the magazine is placed axially displaceably in a supporting tube.

8. The magazine according to claim 1, wherein a partition isolating a pocket from the rest of the chamber is placed in each chamber and at least one through hole is disposed in the wall around this pocket that is closed when the chamber is detachably closed and that is opened when the chamber is opened.

9. The magazine according to claim 8, wherein the concave face, which is made in each chamber a distance above the concave face thereof, is made on the partition.

10. The magazine according to claim 1, wherein on each supporting wall is made a skirt extending along the axis in the opposite direction of the concave face of the supporting wall, and that the skirt is detachably connected to at least the first supporting wall in this direction and/or to the skirt of this wall.

11. A package for keeping a contact lens comprising:
    a supporting wall with a concave face fitting the convex side of the contact lens;
    a skirt made on the supporting wall and extending along an axis in the opposite direction of the concave face; and
    a cap that detachably joins the skirt that collectively define a chamber for retaining the contact lens;
    wherein a number of packages are assembled into a magazine with the cap of each package pressed into the skirt of an adjacent package.

12. A magazine for a package according to claim 11, wherein the base of the cap is made with a convex projection that is in sufficiently close to the concave face of the supporting wall that the contact lens in the chamber is kept dimensionally stably in place between the convex projection and the concave face.

13. A method for taking a contact lens out of a magazine which is displaceably placed in a supporting tube and comprised of a number of supporting walls with skirts detachably pressed together in a row, and together with the supporting walls defining a number of fluid-filled chambers each containing a contact lens, wherein the supporting tube is orientated with the skirts pointing downwards, comprising:
    pushing on the top supporting wall in the row so that the skirt of of the lowest supporting wall will be extending at least partly out of the bottom opening of the supporting tube; and
    removing the lowest supporting wall with the contact lens in the overlying chamber from the supporting tube so the that the contact lens, which due to the moisture present is adhered to the supporting wall, is applied in an eye, and so that the supporting wall is then placed at the top in the supporting tube.

14. The method the claim 13, wherein the removing is accomplished by sticking a finger into the skirt of the supporting wall.

15. A method for applying a contact lens in a package to an eye, wherein the package comprises a supporting wall with a skirt and a cap that detachably joins the skirt of the supporting wall to define a chamber for retaining the contact lens, whereby a number of these packages are assembled in a row with the cap of each package pressed into the skirt of the adjacent package, comprising:

orienting the package row with the caps pointing relatively upwards;

removing the top cap to provide an uncovered chamber;

guiding the package row up towards the eye so that the contact lens in the uncovered chamber is applied; and pressing the cap in place on the supporting wall which then is placed at the bottom in the package row with the cap pressed into the skirt of the overlying supporting wall.

* * * * *

UNITED STATES PATENT AND TRADEMARK OFFICE
CERTIFICATE OF CORRECTION

PATENT NO. : 6,471,052 B2
DATED : October 29, 2002
INVENTOR(S) : Faxe

It is certified that error appears in the above-identified patent and that said Letters Patent is hereby corrected as shown below:

<u>Title page,</u>
Item [75], Inventors, change "Faxe et al." to -- Faxe --.
Change "Inventors" to -- Inventor --, and
Delete "Per Faxe, Svinggårdsven 1, 3100 Hornbaek (DK)".
Item [73], Assignees, change "Hornçk (DK)" to -- Hornbæk (DK) --.

<u>Column 8,</u>
Line 56, delete the second occurrence of the word "of".
Line 61, delete the first occurrence of the word "the".

Signed and Sealed this

Twenty-fifth Day of February, 2003

JAMES E. ROGAN
*Director of the United States Patent and Trademark Office*